United States Patent [19]

Stautzenberger et al.

[11] 4,158,020

[45] Jun. 12, 1979

[54] HYDROFORMYLATION OF OLEFINS

[75] Inventors: Adin L. Stautzenberger; James L. Paul; Jerry D. Unruh, all of Corpus Christi, Tex.

[73] Assignee: Celanese Corporation, New York, N.Y.

[21] Appl. No.: 828,123

[22] Filed: Aug. 26, 1977

Related U.S. Application Data

[63] Continuation of Ser. No. 526,298, Nov. 22, 1974.

[51] Int. Cl.$^2$ ............................................. C07C 45/08
[52] U.S. Cl. ........................................... 260/604 HF
[58] Field of Search ................................. 260/604 HF

[56] References Cited

U.S. PATENT DOCUMENTS

| 3,404,188 | 10/1968 | Privette et al. | 260/617 |
|---|---|---|---|
| 3,511,880 | 5/1970 | Booth | 260/604 HF |
| 3,560,539 | 2/1971 | Booth | 260/429 |

*Primary Examiner*—Werren B. Lone

[57] ABSTRACT

Olefins are converted to aldehydes and/or alcohols having one more carbon atom than the olefin by reacting the olefin with carbon monoxide and hydrogen in the presence of an in situ formed catalytic complex of a Group VIII metal, carbon monoxide and a trivalent ligand, the metal being introduced into the reaction zone in the form of a solution of a water-soluble inorganic salt dissolved in a solvent comprised of at least 40% by volume of a polyalkylene glycol, the polyalkylene glycol acting as a coupling agent preventing precipitation of the metal prior to formation of the catalyst complex.

6 Claims, No Drawings

HYDROFORMYLATION OF OLEFINS

This is a continuation of application Ser. No. 526,298, filed Nov. 22, 1974.

BACKGROUND OF THE INVENTION

Processes for converting olefins to aldehydes and/or alcohols by the reaction of an olefin with carbon monoxide and hydrogen in the presence of a suitable catalyst in either batch or continuous processes are well known in the prior art, and are commonly known as oxo or hydroformylation processes. Many of these reactions require the use of exceedingly high pressures to maintain catalyst stability, particularly when a cobalt carbonyl catalyst is employed.

U.S. Pat. No. 3,239,566 to Slaugh et al and similarly, U.S. Pat. No. 3,527,809 to Pruett et al. and U.S. Pat. No. 3,511,880 to Booth, describe processes for the hydroformylation of olefins in which the necessity of using these high pressures is avoided by employing as a catalyst a complex of Group VIII noble metal, carbon monoxide and a ligand. The preferred metal is rhodium, while the ligand is preferably a trivalent organophosphorus compound, especially a phosphite or phosphine. It is disclosed that the catalytic complex may be pre-formed by combining an organic or inorganic salt of the metal with the desired ligand in liquid phase, then reducing the valence state of the metal and forming the metal-containing complex by heating the solution in an atmosphere of admixed hydrogen and carbon monoxide. It is also taught that the reduction may be performed prior to the use of the catalyst or may be accomplished in situ by heating the metal salt in admixture with the ligand in the presence of both hydrogen and carbon monoxide. Also, the catalyst may be formed by heating a rhodium carbonyl with the phosphorus-containing ligand.

Of these alternatives, the most economical and efficient, particularly in a continuous process, is the in situ formation of the catalyst by introduction of the Group VIII metal salt and ligand into the reaction vessel along with the olefin, hydrogen and carbon monoxide. In practice, however, the alternative tends to be of limited practicality when using the economically available inorganic metal salts, especially the water-soluble inorganic salts of rhodium, since a portion of the metal may be reduced by the hydrogen present in the reaction vessel prior to formation of the metal-carbon monoxide-ligand complex. As a result, a precipitate of elemental metal and/or undesirable metal derivatives is formed in the reaction vessel necessitating frequent purging. Moreover, it is necessary to replenish the metal lost in this manner, thus significantly increasing the operational costs of the process.

SUMMARY OF THE INVENTION

The present invention resides in a modification of the conventional hydroformylation process in a manner permitting in situ formation of these catalysts from commercially available water-soluble Group VIII metal inorganic salts, thus utilizing the commercial advantages of this alternative without the concomitant formation of undesirable precipitates.

More specifically, the process of the present invention comprises introduction of the inorganic Group VIII metal salt into the reaction vessel in the form of a solution of the salt dissolved in a lower polyalkylene glycol, as hereinafter further defined, the lower polyalkylene glycol comprising at least forty percent of the total solution, and acting as a coupling agent to prevent precipitation of the Group VIII metal prior to formation of the catalyst complex.

It is, therefore, the primary object of the present invention to provide an improved process for the hydroformylation of olefins in which the metal-carbon monoxide-ligand-hydrogen catalyst is formed in situ, the metal being introduced into the reaction vessel in the form of a water-soluble inorganic metal salt dissolved in a solvent comprised of at least 40% of a polyalkylene glycol. Another object of the invention is to provide a continuous process of this nature. Other objects of the present invention, if not specifically set forth herein, will be obvious to the skilled artisan upon reading the detailed description of the invention which follows.

DETAILED DESCRIPTION OF THE INVENTION

In general, the present process involves the introduction into a common reaction vessel or zone of the olefin to be hydroformylated, a gaseous mixture of hydrogen and carbon monoxide and the components for forming a catalyst in situ, i.e., a Group VIII metal and a ligand to be complexed therewith, the metal being introduced into the reaction zone as a solution of a water-soluble inorganic salt in a specified solvent. Within the reaction chamber, the metal combines with the ligand, the carbon monoxide and the hydrogen to form the catalyst complex. This complex then catalyzes the hydroformylation of the olefin with the hydrogen and carbon monoxide, thus forming a mixture of aldehydes and/or alcohols containing one more carbon atom than the olefin reactant.

In the detailed description, reference will often be made to practice of the invention using rhodium as the Group VIII metal since rhodium, because of its greater catalytic activity, is preferred in reactions of this type. It is to be understood, however, that the invention may also be practiced using other Group VIII metals, e.g., ruthenium, cobalt, osmium and palladium.

As previously mentioned, the solvent employed as a coupling agent in the present process is comprised of at least about 40% of a lower polyalkylene glycol. Preferably, the polyalkylene glycol is selected from compounds defined by the following formula and mixtures thereof:

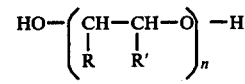

wherein n is 1–3, and R and R' are selected from the group consisting of H and CH$_3$. Most preferably, the polyalkylene glycol is selected from the group consisting of ethylene glycol, diethylene glycol, triethylene glycol, propylene glycol, dipropylene glycol and tripropylene glycol.

While the coupling solvent may consist entirely of one or more of the aforesaid polyalkylene glycols, it is only necessary that the solvent be comprised of at least about forty percent of these glycols in order to prevent significant precipitation of the metal from solution upon exposure to hydrogen within the reaction vessel. The remainder of the solvent used may be comprised of other solvents compatible with the polyalkylene glycol employed, with water and lower alcohols such as ethanol and propanol being especially suitable. Also, commercially available aqueous metal salt solutions, e.g., a 10–20% $Rh(NO_3)_3$ aqueous solution, may be used with the water serving as a portion of the solvent mixture.

Since the anionic portion of the Group VIII metal salt does not enter into the formation of the catalytic complex, the salt may be selected from a number of inorganic salts including, for example, $RhCl_3 \cdot 3H_2O$, $Rh(NO_3)_3$ (aqueous solution), $Rh_2(SO_4)_3$ (aqueous solution), $RhPO_4$ (aqueous solution), $Co(NO_3)_2 \cdot 6H_2O$, $CoBr_2$ (aqueous solution), $Pd(NO_3)_2$ (aqueous solution) $Fe(NO_3)_3 \cdot 9H_2O$, $FeCl_2 \cdot 4H_2O$, $FeSO_4 \cdot 7H_2O$, $IrCl_3$ (aqueous solution), $OsCl_3$ (aqueous solution), $NiCl_2 \cdot 6H_2O$ and $Ni(NO_3)_2 \cdot 6H_2O$. The water soluble rhodium nitrates, chlorides, sulfates, perchlorates, and sulfonates, are especially preferred.

The concentration of rhodium salt dissolved in the coupling solvent is not critical, although it is not always possible to avoid the undesired precipitation of part of the rhodium after introduction of the coupling solvent-rhodium mixture into the hydroformylation reaction medium if the concentration of rhodium salt, calculated as the metal, is much greater than about 2 grams per 100 grams of coupling solvent prior to introduction into the hydroformylation reactor. Successful incorporation of the rhodium into the hydroformylation reaction medium has sometimes been observed at concentrations higher than the 2 grams per 100 grams of coupling solvent, but the behavior of the system with respect to precipitation of rhodium (as salt or as the metal) after introduction of the makeup rhodium into the hydroformylation reaction medium is erratic at concentrations greater than about 2 grams per 100 grams as just explained. The reason for this erratic behavior at higher concentrations is not known with certainty, although an adverse effect due to the presence of water in the coupling solvent may be a factor. More specifically, rhodium nitrate is commonly obtained as aqueous solution, so that some adventitious water is normally present along with the rhodium. In any event, by restricting the rhodium concentration to this maximum of about 2 grams calculated as rhodium metal per 100 grams of coupling solvent, difficulties due to occasional rhodium precipitation upon introduction into the hydroformylation reaction medium are avoided. Normally, from about 0.01 gram to about 2 grams of rhodium, calculated as the metal, are employed in making up the solution of rhodium salt in the coupling solvent. More usually, from about 0.2 to about 1.0 grams of rhodium per hundred grams of solvent will be used.

Suitable ligands for use in the present invention are described in the prior hydroformylation art and are selected from trivalent organo phosphorus, arsenic and antimony compounds, of which the triorgano phosphorus ligands are especially useful. Preferably, the ligand is selected from the group consisting of the triarylphosphites, the triarylphosphines, the trialkylphosphites, and the tricycloalkylphosphites. Triphenylphosphine and triphenylphosphite are particularly suitable. Other suitable ligands may be readily ascertained from the available literature.

A wide variety of olefins, especially olefins having up to about 25 carbon atoms, can be hydroformylated in accordance with the improved process of this invention to form aldehyde and/or alcohol derivatives of said olefins having at least one additional carbon atom as compared with the parent olefin (di- or tri-ethylenically unsaturated olefins being capable, of course, upon complete hydroformylation of forming derivatives having up to 1 additional carbon atom for each ethylenic double bond in the parent compound). Olefinic compounds having substituent groups, e.g., ethylenically unsaturated alcohols, aldehydes, ketones, esters, carboxylic acids, acetals, ketals, nitriles, amines, etc., can also be hydroformylated. Broadly, olefinic compounds which are free of substituent atoms other than oxygen and nitrogen are readily hydroformylated, especially such compounds having no substituent atoms other than oxygen. Some specific classes of substituted olefins to which the hydroformylation process is applicable are: unsaturated aldehydes such as acrolein and crotonaldehyde; alkenoic acids such as acrylic acid; and unsaturated acetals, such as acrolein acetal. More commonly, employed feedstocks include simple alkenes such as ethylene, propylene, the butylenes, etc.; alkadienes such as butadiene and 1,5-hexadiene, and their aryl, alkaryl, and aralkyl derivatives. Hydroformylation does not normally take place within the benzene ring of olefins having aryl substitution of course, but rather in the ethylenically-unsaturated portion of the molecule.

Process operating parameters employed in the present invention will vary depending upon the nature of the end product desired, since variation of operating conditions will vary the ratio of aldehydes to alcohols produced as well as the ratio of normal to isomeric compounds. In general, the operating parameters contemplated by the present process are the same as those conventionally employed in prior art hydroformylation processes. For the sake of convenience, these parameters will be generally described hereinafter; it being understood, however, that the parameters are not critical to achieving the improved results of the present invention and do not per se form a part of the present invention.

In general, the hydroformylation process is conducted under a total reaction pressure of hydrogen and carbon monoxide of one atmosphere or less up to a pressure of about 1000 psia or more. For commercial reasons, however, pressures significantly greater than about 500 psia will not normally be employed.

The reaction is also normally conducted at a temperature of from about 50° to about 200° C. with a temperature within the range from about 75° to about 150° C. being most usually employed.

As is appreciated in the prior art, ligand in excess of the amount required to form the metal-carbonyl-ligand complex is preferably employed in order to achieve optimum reaction conditions. More specifically, it is generally desirable to employ at least about 2 moles of free ligand per mole of metal, with from about 5 to about 500 or more moles of free ligand normally being employed.

The ratio of partial pressures of the hydrogen to carbon monoxide present in the reaction vessel may be from about 10:1 to 1:10, but will normally be from about 3:1 to about 1:3, with a hydrogen to carbon monoxide ratio of at least about 1:1 being preferred.

The metal salt-polyalkylene glycol solution will generally be added to the reaction zone in an amount sufficient to provide about 0.01 g to about 40 g of metal per liter of catalyst solution and preferably from about 0.1 to about 2.0 g. Thus, when using the solutions defined above, at least about 0.5 and preferably from about 10.0 g to about 100.0 g of metal salt-polyalkylene glycol solution per liter of catalyst solution will be introduced into the reaction zone.

If desired, the reaction mixture may also contain other materials, such as an organic solvent to act as a reaction medium for the olefin and the oil-soluble catalytic complex. Additional organic solvents are not required, however, since the olefin reactant also serves as a solvent. Also, the reaction mixture may comprise an alkaline material such as ammonium hydroxide.

The following examples are presented as illustrative of the invention and are not to be taken in limitation thereof.

EXAMPLE I

To demonstrate the effectiveness of the present process in preventing the precipitation of rhodium, the rhodium was introduced into a reaction zone in the form of rhodium nitrate dissolved in the specified solvents. The reaction zone contained a mixture of triphenylphosphine, aldehydes and startup solvent in the presence of hydrogen, carbon monoxide and propylene.

Addition into the reaction zone of a solvent consisting of 1% rhodium as nitrate in about 50% water and 50% propanol resulted in the precipitation of most of the rhodium charged.

Similarly, addition into the reaction zone of a solution consisting of 1% rhodium as nitrate in about 6% water and 93% ethanol resulted in the precipitation of about half of the rhodium charged.

On the other hand, numerous experiments in which a solution consisting of 1% rhodium as nitrate in about 6% water, 47% diethylene glycol and 47% ethanol was introduced into the reaction zone yielded quantitative formation of the active rhodium complex with no precipitation of rhodium.

EXAMPLE II

To demonstrate the effectiveness of various solvents for aqueous solutions of inorganic rhodium salts, the following tests were conducted:

One ml of 10% aqueous solution of rhodium nitrate was dissolved in 50 ml of diethylene glycol. After one month no precipitation from the transparent solution thus formed was noted. In comparison, a solution prepared using ethanol instead of diethylene glycol as the solvent was initially cloudy and an insoluble rhodium salt precipitated.

The solubility of 5% aqueous acid solution of rhodium sulfate was tested with the following compounds: methanol, ethanol, 1-propanol, 2-propanol, acetone, 2-methoxyethanol, dimethylformamide, dimethylacetamide, dimethyl sulfoxide, ethylene glycol, diethylene glycol and tetraethylene glycol. The aqueous rhodium solution was soluble only in the glycols.

EXAMPLE III

Propylene was hydroformylated to produce a product comprising butyraldehyde in a reaction zone maintained at 115° C. and at pressure of 310 psig. The reaction zone contained propylene, carbon monoxide, and hydrogen at partial pressures of 70, 25, and 110 psia respectively. There was also present an inert liquid reaction medium or solvent, as further explained hereinbelow, which contained triphenylphosphine and rhodium ion in concentrations of 1.3 M and 8 mM respectively. The rhodium was introduced into the reaction zone in the form of a rhodium salt dissolved in a solution comprising a polyalkylene glycol in accordance with the preceding disclosure.

Satisfactory hydroformylation results were obtained, and undesired precipitation of the rhodium catalyst was avoided, when the inert solvent employed in the hydroformylation as just described was any of the following: benzene; toluene; diphenyl ether; the diphenyl-diphenyl ether eutectic normally employed as a high-temperature heat transfer medium; and the high-boiling organic by-products obtained as reaction residues in the production of propanal, butanal, heptanal, and nonanal by conventional hydroformylation techniques. Mixtures of these inert solvents are also successfully employed, as well as the other conventional hydroformylation solvents as known to the existing art.

EXAMPLE IV

Hydroformylation of hexene was similarly conducted in a reaction zone at 115° C. under a pressure of 125 psig, the hexene comprising 2.5 wt% of the liquid reaction mixture. A carbon monoxide:hydrogen ratio of 1:1 was employed. The liquid reaction contained triphenylphosphine in a concentration of 2.0 M along with rhodium in a concentration of 12 mM which was introduced as above.

It is to be understood that many modifications and variations of the foregoing invention may be made without departing from the spirit and scope thereof.

What is claimed is:

1. In a process for hydroformylating an olefin with hydrogen and carbon monoxide in a reaction zone to form aldehydes, alcohols, and mixtures thereof, in which process a catalytic complex comprising rhodium, carbon monoxide, and a ligand selected from the group consisting of trivalent organo phosphorus, arsenic, and antimony compounds is formed in situ, the improvement which comprises:

introducing the rhodium into said reaction zone in the form of a water-soluble inorganic salt dissolved in a solvent comprising at least about 40% of a polyalkylene glycol selected from compounds having the following structure and mixtures thereof:

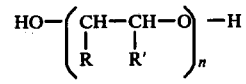

wherein n is 1–3 and R and R' are selected from —H and —CH₃, the remainder of said solvent comprising water and an alcohol selected from the group consisting of ethanol and the propanols, and said inorganic salt being selected from the group consisting of rhodium nitrate, rhodium sulfate, and rhodium phosphate.

2. The process of claim 1 wherein said polyalkylene glycol is diethylene glycol.

3. The process of claim 1 wherein said ligand is selected from the group consisting of the triarylphosphites, the triarylphosphines, the trialkylphosphites, and the tricycloalkylphosphites.

4. The process of claim 1 wherein said olefin contains up to about 25 carbon atoms.

5. The process of claim 1 wherein said inorganic salt is present in an amount of up to about 2 grams, calculated as the metal, per 100 grams of solvent.

6. The process of claim 1 wherein the inorganic salt is rhodium nitrate.

* * * * *